United States Patent [19]
Bobrove et al.

[11] Patent Number: 5,314,503
[45] Date of Patent: May 24, 1994

[54] AUTOMATIC SHEATH PROTECTION OF HYPODERMIC NEEDLE

[75] Inventors: Arthur M. Bobrove, Palo Alto; Robert K. Fernandez, Santa Clara; Thomas C. Robinson, Berkeley; Thomas P. Sahines, Milpitas, all of Calif.

[73] Assignee: Rasor Associates, Inc., Sunnyvale, Calif.

[21] Appl. No.: 35,937

[22] Filed: Mar. 23, 1993

[51] Int. Cl.⁵ ............................................. A61M 29/00
[52] U.S. Cl. ..................................... 604/164; 604/198; 604/263
[58] Field of Search ............... 604/192, 187, 198, 263, 604/110

[56] References Cited

U.S. PATENT DOCUMENTS

| | | |
|---|---|---|
| 3,406,687 | 6/1966 | Moyer . |
| 4,681,567 | 7/1987 | Masters et al. . |
| 4,747,837 | 5/1988 | Hauck . |
| 4,775,369 | 10/1988 | Schwartz . |
| 4,801,295 | 1/1989 | Spencer . |
| 4,973,317 | 11/1990 | Bobrove . |
| 5,151,088 | 9/1992 | Allison et l. .................... 604/192 |

Primary Examiner—John D. Yasko
Attorney, Agent, or Firm—Fliesler, Dubb, Meyer & Lovejoy

[57] ABSTRACT

A hypodermic needle assembly is described which automatically covers the pointed end of the needle after the assembly is used in order to prevent accidental punctures. A sheath circumscribes the needle and is held a patient's tissue to allow sliding movement of the sheath over the needle pointed end, and preferably locking of the needle within the sheath, as well, when the needle is withdrawn from the patient.

29 Claims, 6 Drawing Sheets

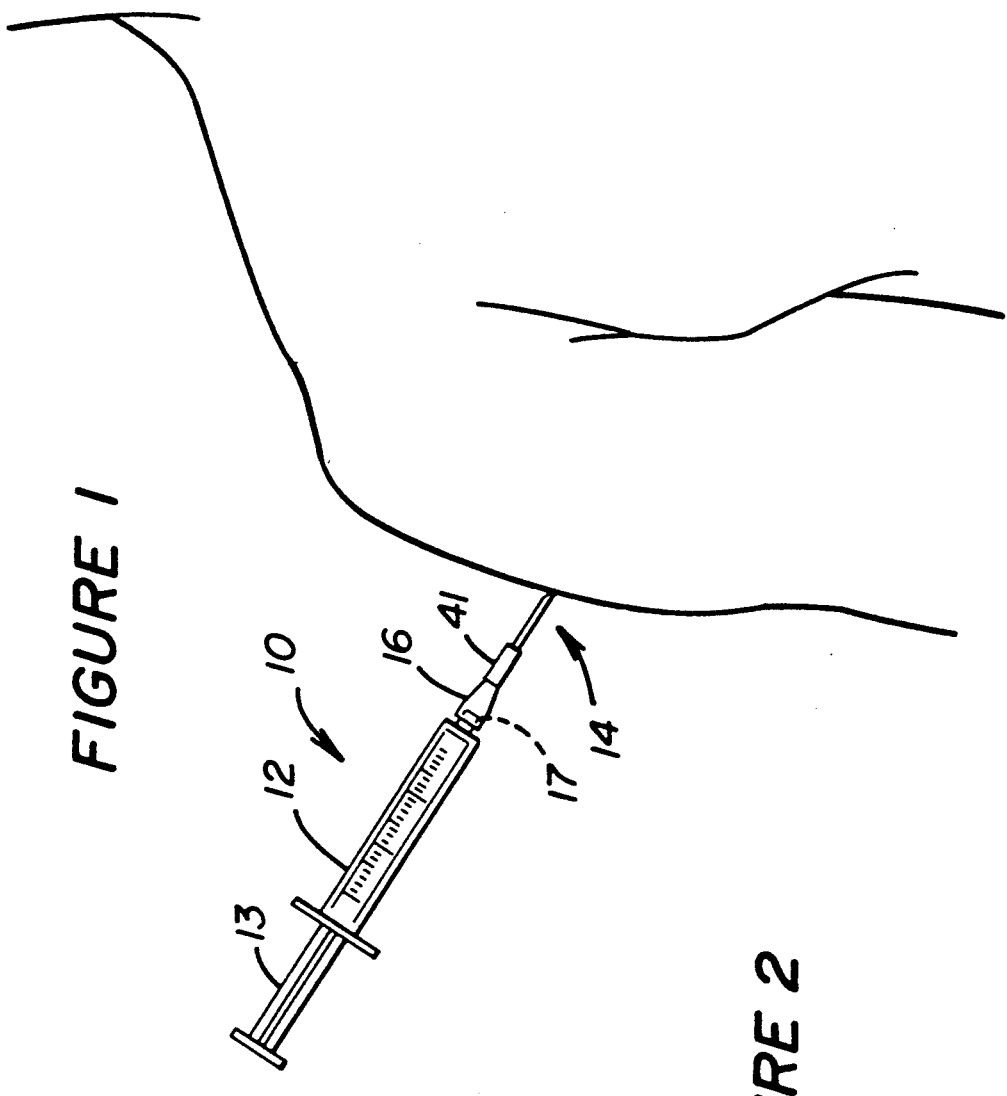

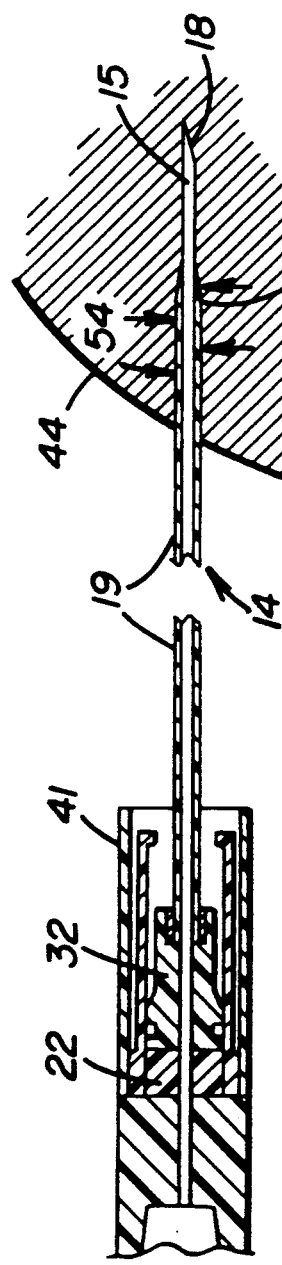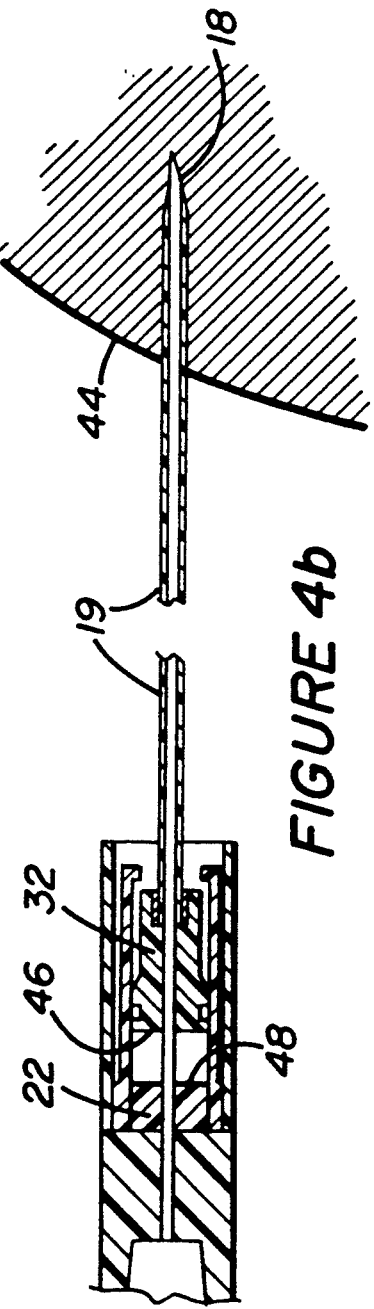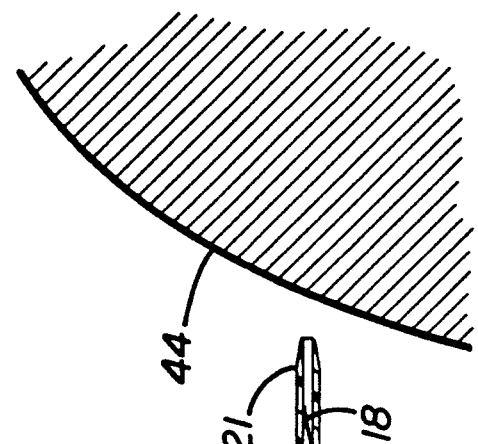

AUTOMATIC SHEATH PROTECTION OF HYPODERMIC NEEDLE

TECHNICAL FIELD

This invention relates generally to a protective assembly for a pointed end of a surgical needle of the type used to pierce the tissue of a patient in order to inject or withdraw fluid from the patient. More particularly, the present invention is related to an assembly having a protective sheath that automatically covers the pointed end of the needle when it is extracted from a patient.

BACKGROUND OF THE INVENTION

Many infectious diseases may be transmitted through an accidental puncture by a contaminated hypodermic needle. The potential for this problem is very high when handling disposable hypodermic needles since they are not sterilized after use and often are not disposed of in a manner which will reduce the likelihood of accidental puncture. Since the advent of Acquired Immune Deficiency Syndrome (AIDS), increasing concern has developed on the subject of the safety of hypodermic needles.

Many designs have been developed for shielding the pointed end of a disposable needle. Some of the designs are automatic and thus do not require manual manipulation. In handling disposable needles, it is the manual capping of a hypodermic needle that poses such a risk since the more a person has to manipulate a needle point, the higher the risk of accidental injury.

In that regard, any design requiring a manual recapping operation presents some risk of an accidental puncture, and moreover, manual recapping of a needle is time consuming. In today's medical environment in which health care workers are already overworked and in short supply, the time spent in recapping a hypodermic needle can be much better utilized on other tasks. Considering the number of times hypodermic needles are used, the total time spent on recapping hypodermic needles is quite significant. In a sense, that represents an inefficient use of resources. Examples of prior designs that required manual manipulation are described in U.S. Pat. Nos. 3,406,687; 4,681,567; 4,747,837 and 4,801,295.

Past automatic designs, on the other hand, are generally complicated, costly to manufacture, and/or prone to defects. As a general rule, the more complex the design, the more expensive the cost of manufacturing, and the more likely it is that the construction will malfunction. An example of an automatic design is described in U.S. Pat. No. 4,775,369.

U.S. Pat. No. 4,973,317 provides a protective construction for a medical needle, particularly a hypodermic needle, that is durable, simple in design and not prone to malfunction. The protective construction includes a sheath which circumscribes the needle in tight-fitting relationship and which has an end portion that penetrates a patient's tissue along with the needle point. The sheath has one or more barbs which interact with a patient's tissue such that extraction of the sheath from the patient is postponed to a time no earlier than extraction of the needle point. In that manner, upon extraction of the sheath from the subject, the needle point is automatically covered by the sheath, thus providing protection against accidental puncture by the needle point after use. Furthermore, such interaction is used to provide the movement necessary to cover the needle point. This patent also discloses the use of a sleeve arrangement which provides a seat for assuring that the sheath follows the needle pointed end in penetrating the patient's tissue. Interaction between the sheath and sleeve locks the sheath in position covering the needle pointed end.

The barbs of the device of U.S. Pat. No. 4,973,317 can, however, be irritating or painful to some patients and/or some medical practitioners may feel that it may cause such irritation and elect not to make use of such a protective construction. Also, production of protective constructions which include such barbs can be difficult and/or expensive.

Some of the above identified problems of automatic type hypodermic needle protective designs are also applicable to those designs requiring manual manipulation. There is much room for improvement.

The present invention is directed to overcoming one or more of the problems as set forth above.

DISCLOSURE OF INVENTION

In accordance with an embodiment of the present invention, a protective assembly is provided for enclosing a used hypodermic needle having a pointed end for piercing tissue of a patient to inject or withdraw fluid from the patient. The assembly automatically provides shielding of the needle pointed end upon extraction of the needle from the patient.

The assembly comprises a sheath circumscribing the needle with a distal end portion of the sheath being adjacent to the pointed end of the needle for piercing the patient's tissue. The sheath and the needle are of a construction such that the sliding frictional force between the external surface of the sheath and the tissue exceeds the sliding frictional force between the internal surface of the sheath and the external surface of the needle (and preferably also the force required to engage a locking mechanism to hold the sheath in place over the needle tip) sufficiently so that when the needle is removed from the tissue the sheath is retained by the patient's tissue until after extraction of the pointed end of the needle from the tissue (and preferably until the locking mechanism has been engaged although this can be accomplished manually). Upon extraction of both the needle pointed end and the sheath from the tissue, the pointed end is automatically disposed within the sheath (and the sheath is preferably locked in place over the needle pointed end).

Sheaths are commonly used on hypodermic needles, especially for vascular access and blood sampling. The presence of a sheath does not increase the pain experienced by a patient as has been demonstrated with actual devices as described herein because the source of the pain results from penetration of the tissue by the needle tip, and not the slight increase in diameter of the needle resulting from the needle being surrounded by the sheath.

The exposed end of the sheath is tapered for easy tissue entry. The sheath is made of a relatively soft material and that fact, along with the sheath having a tapered but comparatively blunt end, prevents skin penetration if substantial forces push it against the skin. This ensures user safety since the sheath tip is exposed to the patient's tissue and blood.

The protective assembly provided by the present invention is durable, simple in design, inexpensive to manufacture, and not prone to malfunction. The protective assembly includes a sheath that circumscribes the needle in a close, but readily slidable, low friction relationship and which has an end portion that penetrates a patient's tissue along with the needle point. The external surface of the sheath is frictionally engaged by the patient's tissue whereupon extraction of the sheath from the patient's tissue is postponed to a time no earlier than extraction of the needle point. In that manner, upon extraction of the sheath from the patient, the needle point is automatically covered by the sheath, thus providing protection against accidental puncture of a person's tissue by the needle point after use. Furthermore, such interaction is used to provide the movement necessary to cover the needle point and preferably to lock the sheath in place. Barbs, which might cause trauma and are difficult and/or relatively expensive to construct, are not needed.

Means for locking the sheath in a position covering the needle point can be provided by a spring and detent mechanism. The locking means utilizes two opposing cantilever beam springs with detents at the free end of the cantilevers. The symmetry of the two opposing cantilevers prevents radial forces from acting between the needle and the sheath, as such forces would increase the static and sliding friction between the needle and the sheath. The material and dimensions of the cantilevers are selected to enable displacement of the free end of each cantilever utilizing a very small radial force. This radial force, which is opposed in balance between the two cantilevers, is preferably made small for enabling the frictional force between a patient's tissue and the sheath to provide enough force to activate the locking mechanism.

Another aspect of the present invention is the ability to implement the present invention using standard hypodermic syringes. The components of the invention can be attached to the hub of a standard syringe, and the components of the invention including the locking means and the sheath can circumscribe a standard hypodermic needle. However, it is generally preferable to use needles specifically designed for the present invention with hubs integrated with the locking components.

A further aspect of the present invention provides a small diameter sheath and a miniature locking mechanism in order to minimize the size increase of a hypodermic needle implementing the present invention. The locking mechanism only slightly increases the length of the total needle assembly, and the sheath only slightly increases the overall diameter of the needle assembly that must penetrate a patient's tissue. By minimizing the dimensions of the overall assembly utilizing the present invention, the needle assembly may be disposed in a "sharps container" along with conventional needles since the container will hold almost as many safety needles as standard needles, but far fewer of the conventional anti-stick devices which are much greater in size than conventional needles.

An additional aspect of the present invention is that the small size and fabrication simplicity of the present invention enables the device to be produced at a relatively low cost.

Other advantages and features of the invention will be described or will become apparent from the following, more detailed description of preferred embodiments.

BRIEF DESCRIPTION OF THE DRAWINGS

The invention will be better understood by reference to the figures of the drawings wherein like numbers denote like parts throughout and wherein:

FIG. 1 is an elevation view illustrating a hypodermic needle with syringe incorporating an embodiment of the invention poised for piercing the arm tissue of a patient;

FIG. 2 is an elevation view, including a cut-away portion, of the present invention wherein the present invention is protecting a human finger from accidental piercing;

FIG. 3c is an end view of the invention shown in and taken along line 3c-3c of FIG. 3a;

FIGS. 4a-4c illustrate various positions of the components of the invention during an injection procedure;

BEST MODE FOR CARRYING OUT INVENTION

Figure 3A:
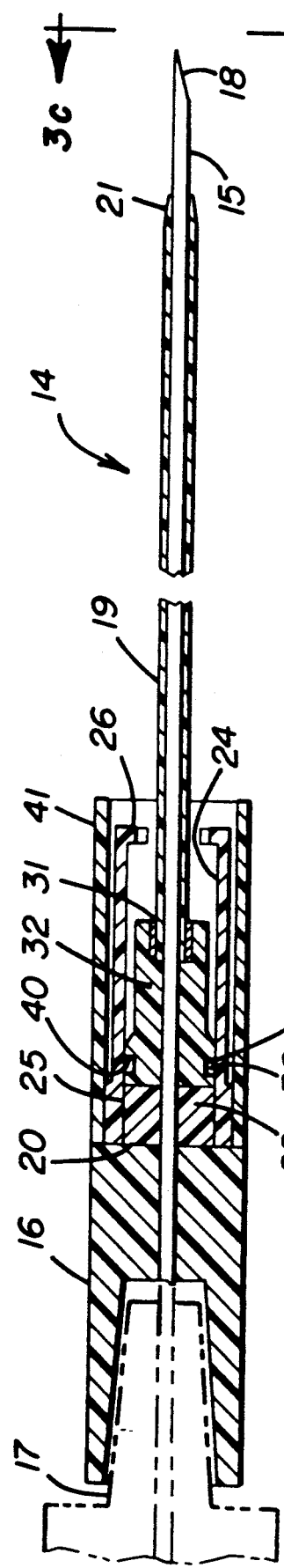
FIG. 3a is a cross-sectional view of a preferred embodiment of the present invention showing the positioning of the components of the invention when the needle pointed end is exposed.

With reference to FIG. 1, a generally conventional syringe 10 is illustrated attached to a protective assembly configured in accordance with the present invention. The syringe 10 includes a tubular body 12 and a plunger 13 for increasing or decreasing the volume within the syringe 10 that is in communication with a hollow, hypodermic needle assembly 14 designed to pierce a patient's tissue.

The needle assembly 14 includes a hollow, stainless steel surgical needle 15 (FIG. 2). The needle assembly 14 also includes a needle hub 16 to facilitate assembly on the hypodermic syringe 10 by insertion of a nozzle 17 of the syringe 10 into the needle hub 16 for communication with the aforesaid volume. The hypodermic or surgical needle 15 includes a sharpened edge 18 (FIG. 2) for penetrating the tissue of a patient. Because the needle 15 is hollow, it acts to provide a pathway for fluid being injected into or withdrawn from a patient.

In accordance with the present invention, automatic sheath protection for a hypodermic needle is provided wherein a sheath circumscribes a hypodermic needle in close fitting but readily slidable relationship with a distal end of the sheath being adjacent to the needle pointed end, wherein retentive friction between a patient's skin tissue and the distal end of the sheath is greater than the readily slidable relationship in order to cause the sheath to slide over and enclose the needle during withdrawal of the needle from a patient's tissue. In that regard, a gap may be present between an inner wall of the sheath and an outer surface of the needle in order to provide the close but readily slidable fit. The close fit between the needle and the sheath enables the sheath to be inserted into the patient along with the needle pointed end without causing significant resistance.

FIG. 2 illustrates the manner in which accidental puncture by the needle pointed end 18 is avoided by a sheath 19. As can be seen in FIG. 2, the needle pointed end 18 is prevented from accidentally puncturing a human finger 11 because the protective sheath 19 has enclosed the needle 15 after an injection procedure. An essential feature of the sheath 19 is that the distal end or tip 21 of the sheath 19 is sufficiently blunt and the material of construction sufficiently soft or flexible so that the tip 21 of the sheath 19 will not itself penetrate the skin of the user or of another person even when relatively high forces are applied to motivate the tip 21 of the needle assembly 14 against a persons skin. Such penetration must be avoided because the sheath 19, in addition to the needle 15, is contaminated by the patient's blood on insertion into the patient. Compressive forces of the sheath tip 21 may occur accidentally with the user pushing the sheath against the users skin, the skin of another person present or another object. The sheath 19 is designed and its material is selected to prevent such forces from exposing the needle sharpened edge 18 and allowing the skin or other object to be accidentally punctured by the sharpened edge 18.

The modulus and strength of the material used for the sheath 19 and its thickness are selected to enable the sheath 19 to resist collapsing, excessive bending or deformation and exposure of the sharpened edge 18 or penetration of the wall of the sheath 19. One suitable material is a tetrafluoroethylene fluorocarbon polymer ('Teflon®', a trademark of Du pont). Polyethylene, polypropylene or more rigid polymers such as polyesters, polycarbonate and polysulfone, as well as other materials can also be utilized.

Figure 3C:
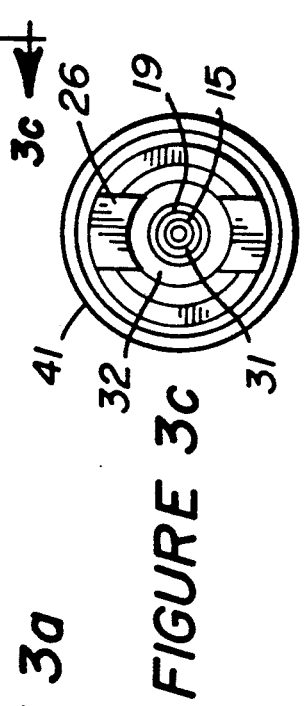
Figure 3B:
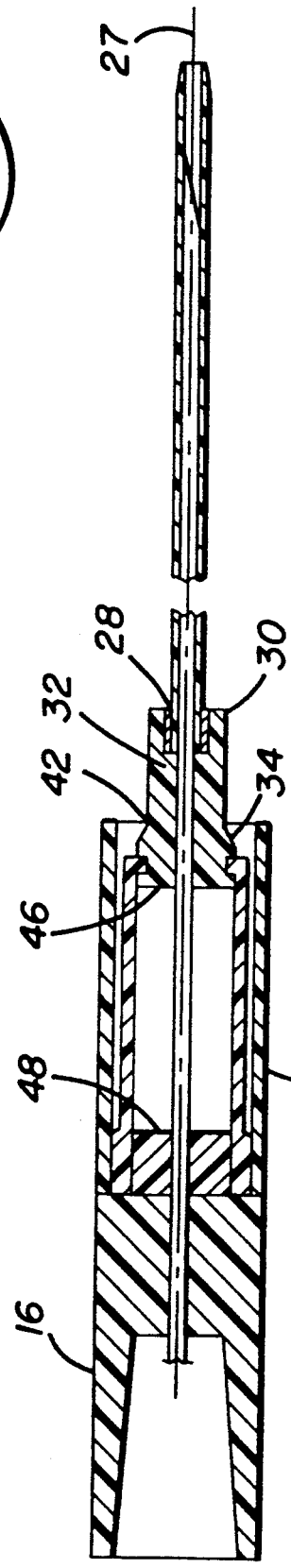
FIG. 3b illustrates the positioning of the components of the embodiment shown in FIG. 3a when the needle pointed end is enclosed by the invention.
Figure 3D:
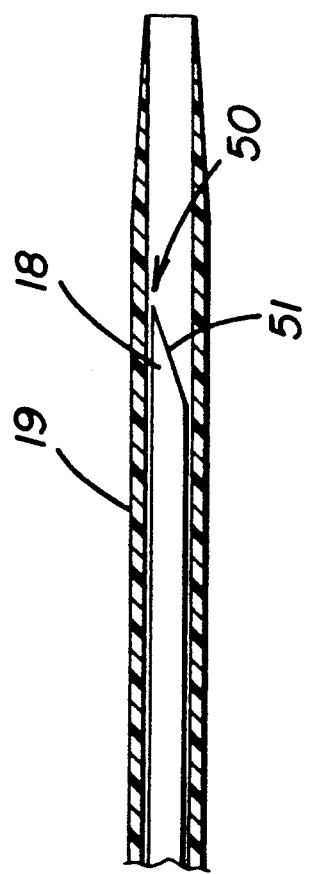
FIG. 3d is an enlarged view of a distal end of the embodiment shown in FIG. 3b.

Turning now to FIGS. 3a and 3b, these illustrations provide cross-sectional views of one preferred embodiment of the present invention. FIG. 3a illustrates the positioning of the components prior to and during insertion of the needle assembly 14 into a patient, and FIG. 3b illustrates the positioning of the components after the needle assembly 14 has been completely withdrawn from the patent. FIG. 3c is an end view of FIG. 3a, and FIG. 3d is an enlarged view of a portion of FIG. 3b.

The needle hub 16 serves for securing the present invention to the nozzle 17 of the syringe 10. A distal end 20 of the needle hub 16 is either rigidly secured to an adapter 22 or may alternatively be unitary with the adapter 22. A pair of opposing cantilever springs 24 each have a first end 25 rigidly secured to the adapter 22. The opposing cantilever springs 24 are substantially parallel to a longitudinal axis 27 of the needle 15. The cantilever springs 24 include detents 26 facing readily inward toward the longitudinal axis 27 in order to balance opposing forces of the cantilever springs 24 and prevent radial forces at the interface between the needle 15 and the sheath 19.

The sheath 19 has a proximal end 28 secured to, or may be insert molded or otherwise made unitary with, a distal end 30 of a cylindrical hub 32. This may be accomplished by including a cylindrical slot 31 in the distal end 30 of the cylindrical hub 32 for inserting the proximal end of the sheath 19. The hub 32 is concentrically and slidably mounted to the needle 15. The cylindrical hub 32 includes a tapered conical lock ramp 34 along which the detents 26 of the cantilevers 24 travel along before entering a circular groove 36 that forms a lock stop 38 and a lock edge 40. The detents 26, lock stop 38 and lock edge 40 may all be angled, tapered or dovetailed to ensure that high axial forces cannot force the detents 26 out of the groove 36. These angles are such that the axial widths of the detents 26 and groove 36 are greater at their smaller diameter.

As the needle pointed end 18 is being withdrawn from the tissue of a patient following an injection or sampling procedure (or if the sheath is grasped and the needle moved distally relatively to the sheath following removal of the needle from the patient's tissue), the cylindrical hub 32 slides towards the detents 26 and the ramp 34 forces the detents 26 apart and increases the radial force between the detents 26 and the ramp 34 generated by the cantilever springs 24. This force is zero at the small diameter end 42 of the conical ramp 34. This force is kept small by an appropriate selection of cantilever modulus of elasticity and dimensions. The axial force between the detents 26 and the ramp 34 is kept very small by keeping the ramp angle small, using smooth surfaced, low-friction materials for the ramp 34 and detents 26 and slightly radiusing or chamfering the detent corners that contact the ramp 34.

It is important to emphasize that an essential requirement of the design of a safety needle configured in accordance with the present invention is that the frictional forces (static and sliding) between the needle 15 and the sheath 19, and preferably the force needed to slide the cylindrical hub 32 into a locked position wherein the detents 26 are positioned within the circular groove 36, as well, must be less than the frictional forces between the patient's tissue and the outer surface of the sheath 19. A reduced frictional force is achieved between the inner surface of the sheath 19 and the outer surface of the needle 15 by providing a very small gap 50 (FIG. 3d) between the sheath 19 and the needle 15 in order to prevent a tight fit and achieve a relatively loose fit, while also utilizing very smooth surfaces on the opposing surfaces of the sheath 19 and the needle 15. Furthermore, the low friction requirement is also achieved by using a sheath material that is inherently slippery, such as Teflon® or polyester material, or using a liquid or solid lubricant on the outside of the needle 15 and/or on the inside of the sheath 19.

The needle assembly 14 most desirably also includes a tubular sleeve 41 which circumscribes both the surgical needle 15 and the sheath 19 in spaced relationship thereto as illustrated. The sleeve 41 is mounted on the adapter 22 non-movably with respect to the surgical needle 15. The tubular sleeve 41 covers the cantilevers 24 to prevent accidental damage or internal manual unlocking of the detents 26 from the circular groove 36 after an injection or sampling procedure (FIG. 3b).

The cantilevers 24 are preferably made of a flexible plastic material. The needle hub 16, adapter 22, cylindrical hub 32, and sleeve 41 are preferably made of a lightweight plastic. The components of the invention can be secured together by gluing, heat welding or insert molding. Some of the components can be combined into unitary structures, e.g., the needle hub 16 can be made integral with the adapter 22.

FIGS. 3a and 3b show the opposing extreme operating positions of the cylindrical hub 32. As can be seen by comparing FIGS. 3a and 3b, the needle 15 is exposed in FIG. 3a, but in FIG. 3b the needle 15 is enclosed by the sheath 19 in order to prevent the needle 15 from accidentally poking the patient or a person handling the syringe assembly 10 after the completion of an injection procedure. As can be seen in FIG. 3b, the cylindrical hub 32 is locked in the distal position, and thus, the sheath 19, which is secured to the hub 32, is locked in position for enclosing the needle 15.

FIG. 3d is an enlarged view of the needle assembly 14, and it provides an enlarged illustration of the gap 50 between the internal surface of the sheath 19 and the external surface of the needle 15. The sheath 19 is formed of a low friction material at least on its inner surface. Note that the external surface of the sheath 19 may be roughened in order to provide somewhat enhanced frictional engagement with a patient's skin tissue. The external surface of the needle 15 may have a coating 51 of a low frictional material, such as a lubricant layer, in order to provide the required readily slidable relationship between the needle 15 and the sheath 19. The coating 51 can be of molecular dimensions and the gap 50 can be substantially zero so long as the required relative frictional relationship is provided.

The distal end 21 of the sheath 19 can be tapered a small extent to facilitate penetration of a patient's tissue with the needle edge 18. The sheath distal end 21 is purposely not sharp or rigid in order to ensure that accidental skin penetration by the sheath distal end 21 cannot occur once the used needle assembly 14 has been removed from a patient. It should be noted that the material of the sheath 19 need not be sufficiently structurally rigid in-and-of-itself to facilitate such penetration — the needle 15 itself can provide the necessary structural strength in view of the close but readily slidable relationship whereby the needle 15 is proximate to the sheath 19, particularly at the sheath first end 21. However, the sheath 19 must be sufficiently strong and rigid to prevent axial compressive forces on the sheath tip 21 from deforming the tip 21 sufficiently to expose the needle sharpened edge 18 or the allow the needle sharpened edge 18 to penetrate through the wall of the sheath 19 if the distal end of the sheath 19 has been bent over.

Basically what is essential in all of the illustrated embodiments is that the sliding frictional engagement force between a patient's tissue and the sheath 19 must exceed the sliding frictional engagement force between the sheath 19 and the needle 15 and, very preferably, the locking mechanism, sufficiently so that the needle 15 can be withdrawn from the sheath 19 and, very preferably, the locking mechanism can be activated while the sheath 19 remains imbedded in a patient's tissue.

Referring now to FIGS. 4a–4c, the various positions of the slidable cylindrical hub 32 and the distal end of the sheath 21 are illustrated that occur during an injection or sampling procedure using the present invention. Referring first to FIG. 4a, the cylindrical hub 32 is positioned at the extreme proximal position adjacent to the adapter 22 as the needle pointed end 18 and the sheath distal end 21 are inserted into the skin and subcutaneous tissue 44 (and muscle for an intermuscular injection of a drug) of a patient. Such insertion or penetration is in response to a force supplied by a health care provider on the syringe 10 that urges the needle pointed end 18 in a direction toward and into the patient's tissue 44. A hypodermic needle 15 incorporating the present invention is inserted into a patient's tissue in the same manner as an ordinary or conventional needle.

As illustrated in FIG. 4a, the distal end 21 of the sheath 19 is inserted along with the surgical needle 15 to penetrate the tissue 44. In this connection, the pointed end 18 provides the initial penetration and leads the way both for the remainder of the needle 15 and the distal end 21 of the sheath 19. As the needle 15 is inserted into the tissue 44 of a patient, the proximal end 46 of the cylindrical hub 32 abuts against a seat 48 of the adapter 22 in order to assure such penetration.

FIG. 4b illustrates the positioning of the components of the invention as the needle 15 is being withdrawn from the patient's tissue 44, and FIG. 4c illustrates the positioning of the components after the needle has been completely withdrawn from the tissue 44. During withdrawal of the needle 15 from the tissue 44, the external surface of the sheath 19 interacts with the patient's tissue 44 for automatically delaying extraction of the sheath 19 until after extraction of the pointed end 18 from the tissue 44. The interaction results from the natural elasticity or resiliency of the tissue 44 and its inherent tendency to close a puncture, as illustrated by the arrows 54, whereby the tissue 44 is urged radially inwardly into a pinching relationship to the sheath 19 thus leading to a frictional force tending to hold the sheath 19 in the wound. Thus, the frictional force resists extraction of the sheath 19 when the needle 15 is extracted in response to the normal needle retraction force provided by the health provider or other person operating the syringe.

As the hypodermic needle 15 is retracted, the sheath 19 retains its position, i.e., the needle 15 slides within the sheath 19 as the needle 15 is retracted. That is why it is important that the close fitting relation between the sheath 19 and the needle 15 be such that ready slidability is provided. A very tight fit could lead to frictional engagement of the internal bore of the sheath 19 with the external surface of the needle 15 whereby the sheath 19 would be extracted along with the needle 15 rather than remaining substantially stationary as the needle 15 is withdrawn.

Means for locking the sheath 19 over the needle pointed end 18 are preferably provided by the cylindrical hub 32 and cantilevers 24. The locking means prevent the sheath 19 from retracting and exposing the needle tip 18, even when substantial force is applied to the tip of the sheath. Moreover, the sheath wall is sufficiently thick and strong to prevent the needle tip 18 from puncturing the sheath 19 when forces (such as finger pressure) are applied to the tip of the sheath.

When the detents 26 are positioned within the groove 30, the lock edge 40 prevents the sheath 19 from sliding towards the hub 16. The lock edge 40 and a facing detent 26 have surfaces essentially perpendicular to the needle axis 27 in order to ensure that the detent 26 is held in place even when a significant force is applied to the distal end 21 of the sheath urging the cylindrical hub 32 towards the seat 48 of the adapter 22. Similarly, the lock stop edge 38 prevents the cylindrical hub 32 from sliding in an opposite axial direction away from the seat 48. Consequently, the sheath 19 is locked in a fixed position relative to the needle tip 18.

Nothing prevents the sheath 19 from moving towards the needle tip 18 except friction. A tip cover may be used in order to ensure that the sheath 19 does not move over the needle tip 18 or enter a locked position while being shipped within a package or when the hub 16 is attached to a syringe prior to use.

The transition between the position shown in FIG. 4a and the position shown in FIG. 4c occurs automatically during an injection or sampling procedure, and there is no additional manipulation required by the health provider to cover the needle pointed end 18.

It should be emphasized that the entire procedure illustrated by FIGS. 4a–4c is identical, from the standpoint of the user, to the standard procedure of injections or samplings with a conventional needle and syringe. No action by the user is needed to achieve protection from unintentional needle sticks, scratches or pokes a distinct feature from other safety needle designs. Furthermore, any standard syringe can be used with this new safety needle, although, as previously discussed, it is preferred that the needle assembly not use a standard needle and hub but instead use a special needle with a hub which forms a part of the assembly and without the need or use of an adapter.

Figure 5:
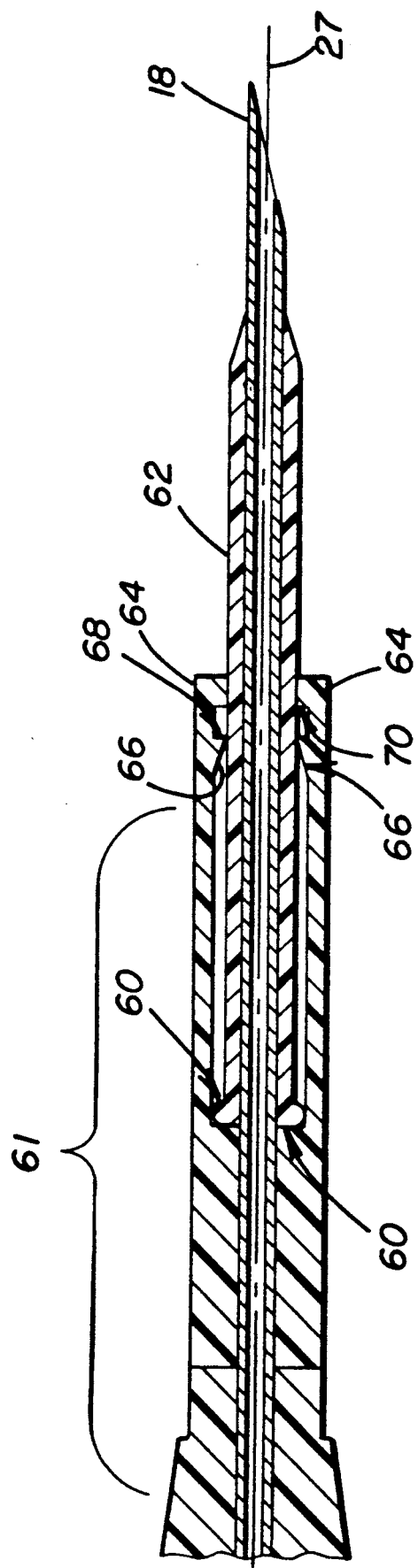
FIG. 5 is a cross-sectional view of another embodiment of the present invention.

FIG. 5 illustrates another embodiment of the present invention, wherein detents 60 are included on the proximal end of the sheath 62. The free end of the cantilever springs 64 incorporate the ramp 66, the lock edge 68, and the lock stop edge 70. Furthermore, the embodiment shown in FIG. 5 incorporates into one, unitary component 61 the hub 16, adapter 22, and cantilevers 24 shown in FIGS. 3a and 3b.

Figure 6:
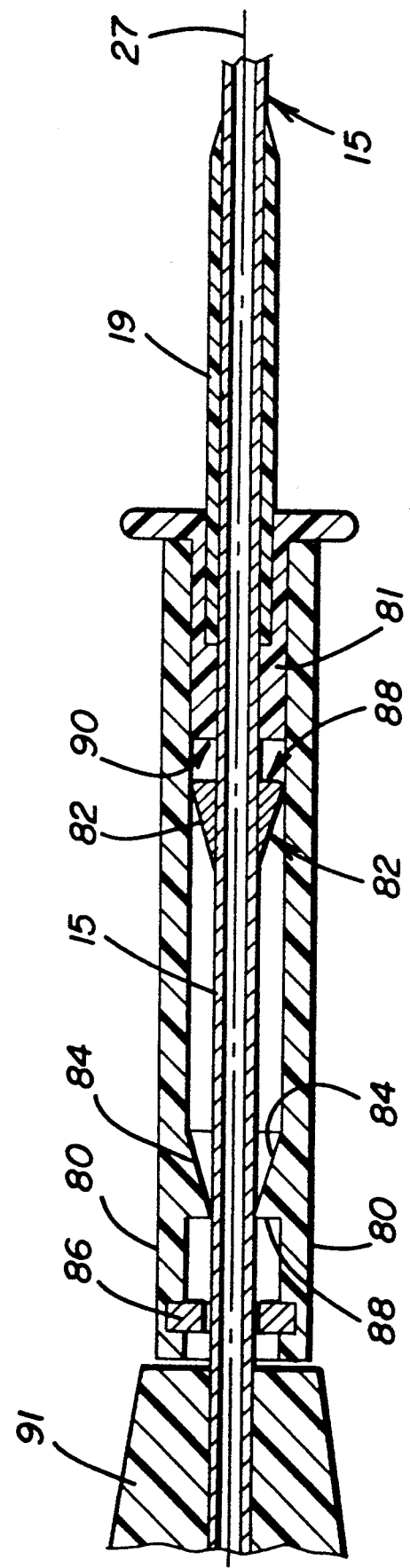
FIG. 6 is a cross-sectional view of a further embodiment of the present invention.

FIG. 6 illustrates a further embodiment of the present invention, wherein the cantilever springs 80 are attached to a sheath hub 81, and not to the needle hub 16 as shown in FIGS. 3a and 3b. This embodiment includes a needle hub 91 for securing the assembly to the distal end of a syringe. A first ramp 82 is attached to the needle 15, and a second ramp 84 is included as part of the cantilevers 80. Lock stops 86 are provided by detents included in the cantilevers 80 and lock edges 88 are provided by opposing ends of the ramps 82 and 84. A seat 90 is provided by the sheath hub 81.

It will be seen from the above discussion regarding the present invention that the pointed end of the needle 15 is automatically disposed within the sheath 19 by the needle extraction force. The patient will experience little or no additional pain because of the penetration by the added sheath 19 and the use of barbs which would interact with the patient's tissue, and which can be difficult to construct, particularly by mass production techniques, is eliminated. A quite efficient and simple means is therefore provided to cover the needle pointed end 18 automatically without any extra manipulation being required by the health provider. It should be noted that the very same forces which traditionally are used by a health provider to both pierce a patient's tissue 44 with a hypodermic needle 15 and to extract the same from the patient, are used to provide the automatic disposal of the needle pointed end 18 in the sheath 19.

INDUSTRIAL APPLICABILITY

The present invention provides a hypodermic needle assembly wherein the needle 15 is inserted along with a covering sheath 19. The assembly includes the feature that the sheath 19 is delayed from exiting the patient until after the needle 15 has been withdrawn sufficiently so that the pointed end 18 of the needle 15 is captured within the sheath 19. A detent mechanism 26 serves to assure retention of the needle 15 within the sheath 19.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

That Which Is Claimed Is:

1. A protective assembly for a medical needle having a pointed end for piercing tissue of a patient to inject or withdraw fluid from the patient, the assembly automatically providing shielding of the needle pointed end upon extraction of the needle from a patient, comprising:

a sheath circumscribing the needle with a distal end portion of the sheath being adjacent to the pointed end of the needle for entering the patient's tissue with the needle in response to a distal force applied into the patient's tissue; and wherein the sheath and the needle are of a retention assembly such that the sliding frictional force between a generally continuous non-radially expanding external surface of the sheath and the tissue exceeds the sliding frictional force between an internal surface of the sheath and an external surface of the needle in a sufficient amount so that, due to such exceeding being in said sufficient amount, the sheath is retained by the patient's tissue as a proximal force is applied outwardly to remove the needle from the patient's tissue until after extraction of the pointed end of the needle from the tissue;

whereby upon extraction of both the needle pointed end and the sheath from the tissue, the pointed end is automatically disposed within the sheath.

2. A protective assembly as recited in claim 1, further including:

locking means for locking the sheath about the needle with the pointed end of the needle encased within the sheath; and wherein the retention assembly is such that the sliding frictional force between the external surface of the sheath and the tissue exceeds the sum of 1) the sliding frictional force between an internal surface of the sheath and an external surface of the needle and 2) the forces which are present as the locking means operates in said sufficient amount so that, due to such exceeding being in said sufficient amount, the sheath is retained by the patient's tissue until after locking of the sheath about the needle with the pointed end of the needle encase within the sheath;

whereby upon extraction of both the needle pointed end and the sheath from the tissue, the pointed end id automatically locked within the sheath.

3. A protective assembly as recited in claim 2 wherein the needle is a hypodermic needle for a hypodermic syringe having a hollow body containing the fluid.

4. A protective assembly as recited in claim 2 wherein the distal and proximal applied forces are respectively also the forces for inserting and withdrawing the needle from a patient's tissue.

5. A protective assembly as recited in claim 4 wherein the sheath is mounted on the needle for sliding movement thereon between a first position at which the needle pointed end projects beyond the sheath end portion and is exposed and a second position at which the needle pointed end is disposed within the sheath.

6. A protective assembly as recited in claim 5 further including first limiting means for preventing sliding motion of the sheath on the needle beyond the first position so that the sheath travels with the needle in response to the distal force.

7. A protective assembly as recited in claim 6, further comprising:

a needle hub to be secured to a distal end of a syringe and a protective assembly carried by the needle hub, and wherein the first limiting means is a seat provided by the needle hub.

8. A protective assembly as recited in claim 5 further including lock means to prevent the sheath from returning toward the first position to expose any needle pointed end after the same is disposed within the sheath.

9. A protective assembly as recited in claim 2 further including stop means to assure withdrawal of the sheath from the patient's tissue after the needle pointed end is disposed within the sheath.

10. A protective assembly as recited in claim 7 further including a cantilever attached at a first end to the needle hub, a cylindrical hub circumscribing and slidably mounted to the needle and attached to the proximal end of the sheath, an indent on one end of the cylindrical hub and a detent on a second end of the cantilever, the indent and detent providing the locking means and the stop means.

11. A protective assembly as set forth in claim 2, wherein the retention assembly is provided by a gap between the internal surface of the sheath and the external surface of the needle.

12. A protective assembly as set forth in claim 2, wherein the distal end portion of the sheath is in close fitting relation to the pointed end of the needle.

13. A protective assembly as set forth in claim 2, wherein the retention assembly is provided by utilizing low friction materials for at least one of the internal surface of the sheath and the external surface of the needle.

14. A protective assembly as set forth in claim 13, wherein the low friction material is provided as a coating on the external surface of the needle or on the internal surface of the sheath.

15. A protective assembly for a hypodermic assembly needle to inject or withdraw fluid from a patient, the assembly having both a hollow needle having a pointed end for piercing the tissue of a patient and a hollow body for containing the fluid in communication with the needle, the assembly automatically providing shielding of the needle pointed end upon extraction of the needle from a patient, comprising:

a sheath circumscribing the needle with a distal end portion of the sheath being adjacent to the pointed end of the needle for piercing the patient's tissue with the needle in response to a distal force applied into the patient's tissue;

wherein the sheath and the needle are of a retention assembly such that the sliding frictional force between an external surface of the sheath and the tissue exceeds the sliding frictional force between an internal surface of the sheath and an external surface of the needle the forces which are present as the locking in an amount sufficient so that, due to such exceeding being in said sufficient amount, the sheath is retained by the patient's tissue as a proximal force is applied outwardly to remove the needle from the patient's tissue until after extraction of the pointed end of the needle from the tissue; and whereby upon extraction of both the needle pointed end and the sheath from the tissue, the pointed end is automatically disposed within the sheath.

16. A protective assembly as recited in claim 15, further including:

locking means for locking the sheath about the needle with the pointed end of the needle encased within the sheath;

wherein the retention assembly is such that the sliding frictional force between the external surface of the sheath and the tissue exceeds the sum of 1) the sliding frictional force between the internal surface of the sheath and the external surface of the needle and 2) the forces which are present as the locking means operates in said sufficient amount so that, due to such exceeding being in said sufficient amount, the sheath is retained by the patient's tissue as a proximal force is applied outwardly to remove the needle from the patient's tissue until after locking of the sheath about the needle with the pointed end of the needle encased within the sheath; and whereby upon extraction of both the needle pointed end and the sheath from the tissue, the pointed end is automatically locked within the sheath.

17. A protective assembly as recited in claim 16 wherein the distal and proximal applied forces are respectively also the forces for inserting and withdrawing the needle from a patient's tissue.

18. A protective assembly as recited in claim 17 wherein the sheath is mounted on the needle for sliding movement thereon between a first position at which the needle pointed end projects beyond the sheath end portion and is exposed and a second position at which the needle pointed end is disposed within the sheath.

19. A protective assembly as recited in claim 18 further including first limiting means for preventing sliding motion of the sheath on the needle beyond the first position so that the sheath travels with the needle in response to the first applied force.

20. An assembly for protecting a person from an unintentional puncture by a distal pointed end of a used hypodermic needle, wherein the protective assembly is to be secured to the distal end of a medical syringe, said protective assembly comprising:

a needle hub having a proximal end to be secured to the distal end of a medical syringe;

a hypodermic needle secured to the needle hub, wherein the hypodermic needle includes a hollow passage for communication liquid between and through a proximal end and the distal pointed end of the hypodermic needle;

a sheath circumscribing and slidably mounted to an external surface of the hypodermic needle, wherein a distal end of the sheath is proximate to the distal pointed end of the hypodermic needle, and the distal end of the sheath and the distal pointed end of the hypodermic needle are to both penetrate a patient's tissue; and locking means for locking the sheath about the needle with the pointed end of the needle encased within the sheath; and wherein a first frictional force existing between the external surface of the hypodermic needle and an internal surface of the sheath is less than 1) a second frictional force created between an external surface of the sheath and the patient's tissue when the sheath and hypodermic needle are inserted into the patient's tissue and 2) the forces created as the locking means operates, and the greater second frictional force is greater than the first frictional force in a sufficient amount such that, due to the magnitude of said sufficient amount, the sheath is caused to slide over the distal pointed end as the sheath and hypodermic needle are withdrawn from the patient's tissue.

21. The protective assembly as defined in claim 20, wherein the second frictional force is created by elastic tendency of a patient's tissue to close around a penetrating hypodermic needle.

22. The protective assembly as defined in claim 20, wherein the sheath slides between a proximal position in which the distal point end of the hypodermic needle is exposed, and a distal position in which the distal pointed end of the hypodermic needle is covered by the sheath.

23. The protective assembly as defined in claim 20, further comprising:
a syringe having a distal end secured to the proximal end of the needle hub.

24. An assembly for protecting a person from an unintentional puncture by a distal pointed end of a used hypodermic needle, wherein the protective assembly is to be secured to the distal end of a medical syringe, said protective assembly comprising:
a needle hub having a proximal end to be secured to the distal end of a medical syringe;
a hypodermic needle secured to the needle hub, wherein the hypodermic needle includes a hollow passage for communication liquid between and through a proximal end and the distal pointed end of the hypodermic needle;
a sheath circumscribing and slidably mounted to an external surface of the hypodermic needle, wherein a distal end of the sheath is proximate to the distal pointed end of the hypodermic needle, and the distal end of the sheath and the distal pointed end of the hypodermic needle are to both penetrate a patient's tissue; and
locking means for locking the sheath about the needle with the pointed end of the needle encased within the sheath;
wherein a first frictional force existing between the external surface of the hypodermic needle and an internal surface of the sheath is less that 1) a second frictional force created between an external surface of the sheath and the patient's tissue when the sheath and hypodermic needle are inserted into the patient's tissue and 2) the forces created as the locking means operates, and the greater second frictional force caused the sheath to slide over the distal pointed end as the sheath and hypodermic needle are withdrawn from the patient's tissue; and further including:
a cylindrical hub circumscribing and mounted to the hypodermic needle so as to slide between proximal and distal sliding positions, wherein a proximal end of the sheath is secured to the cylindrical hub, and the cylindrical hub includes a groove circumscribing the cylindrical hub; and
a flexible cantilever spring having a first end rigidly secured to the needle hub and a second free end including a detent sized to fit within the groove of the cylindrical hub, wherein the detent engages the groove when the cylindrical hub is in the distal sliding position in order to lock the sheath over the distal pointed end of the needle.

25. The protective assembly as defined in claim 24, wherein the needle hub includes a seat and a proximal end of the cylindrical hub is positioned against the seat when cylindrical hub is in the proximal sliding position and the distal pointed end of the needle and the sheath are being inserted into the tissue of a patient.

26. An assembly for protecting a person from an unintentional puncture by a distal pointed end of a used hypodermic needle, wherein the protective assembly is to be secured to the distal end of a medical syringe, said protective assembly comprising:
a needle hub having a proximal end secured to the distal end of a medical syringe;
a hypodermic needle secured to the needle hub, wherein the hypodermic needle includes a hollow passage for communication liquid between and through a proximal end and the distal pointed end of the hypodermic needle;
a sheath circumscribing and slidably mounted to an external surface of the hyppodermic needle, wherein a distal end of the sheath is proximate to the distal pointed end of the hypodermic needle, and the distal end of the sheath and the distal pointed end of the hypodermic needle are to both penetrate a patient's tissue; and
locking means for locking the sheath about the needle with the pointed end of the needle encased within the sheath;
wherein a first frictional force existing between the external surface of the hypodermic needle and an internal surface of the sheath is less than 1) a second frictional force created between an external surface of the sheath and the patient's tissue when the sheath and hypodermic needle are inserted into the patient's tissue and 2) the forces created as the locking means operates, and the grater second frictional force causes the sheath to slide over the distal pointed end as the sheath and hypodermic needle are withdrawn from the patient's tissue;
wherein the cylindrical hub includes a first portion having a smaller diameter and a second portion having a larger diameter, and a ramped portion between the first and second diameter portions, and wherein the groove is positioned within the second portion so that the detent of the cantilever slides against the ramped portion in order to engage the groove and lock the cylindrical hub in the distal sliding position and prevent the cylindrical hub from returning to the proximal sliding position.

27. The protective assembly as defined in claim 24, further comprising:
a tubular sleeve secured to the adapter and covering the cantilever spring in order to protect the cantilever spring and prevent the detent from being manually removed from the groove once engaged.

28. A protective assembly to be secured to a nozzle of a medical syringe, said protective assembly comprising:
a needle hub adapted to be secured to the nozzle of the medical syringe, the hub including at least a pair of cantilever springs each having a first end rigidly secured to the needle hub and a second free end;
a hypodermic needle having a proximal end and a distal pointed end, the hypodermic needle being secured to the needle hub, and the hypodermic needle including a hollow passage for communication liquid between and through the proximal end and the distal pointed end of the hypodermic needle, and each second free end of each cantilever spring includes a slot at a distal end of the cantilever spring that is transverse to the hollow passage of the hypodermic needle;
a sheath circumscribing and slidably mounted around an external surface of the hypodermic needle and capable of sliding between proximate and distal sliding positions, wherein a distal end of the sheath is proximate to the distal pointed end of the hypodermic needle, and the distal end of the sheath and the distal pointed end of the hypodermic needle are to both penetrate a patient's tissue, and the sheath further includes detents on a proximal end of the sheath that are to engage the slots of the cantilever springs and lock the sheath in the distal sliding position; and a first frictional force existing between the external surface of the hypodermic needle and an internal surface of the sheath being less than the sum of 1) a second frictional force to be created between an external surface of the sheath and the patient's tissue when the sheath and hypodermic needle are inserted into the patient's tissue and 2) the forces to be created as the cantilever springs and detents lock the sheath about the needle, and the greater second frictional force causes the sheath to slide over the distal pointed end as the sheath and hypodermic needle are withdrawn from the patient's tissue and the sheath is locked in the distal sliding position.

29. The protective assembly as defined in claim 28, wherein the hub further includes a seat and the proximal end of the sheath is positioned against the seat when the sheath is in the proximal sliding position and the distal pointed end of the needle and the distal end of the sheath are penetrating a patient's tissue.

* * * * *

UNITED STATES PATENT AND TRADEMARK OFFICE
CERTIFICATE OF CORRECTION

PATENT NO. : 5,314,503
DATED : May 24, 1994
INVENTOR(S) : Bobrove et al.

It is certified that error appears in the above-indentified patent and that said Letters Patent is hereby corrected as shown below:

Col. 4, line 19, after "FIG." and before "the", delete "3awhen" and insert therefor --3a when--.
Col. 10, lines 47-48, after "end" and before "automatically", delete "id" and insert therefor --is--.
Col. 11, lines 57-58, after "needle" and before "in", delete "the forces which are present as the locking".
Col. 12, line 44, after "for" and before "liquid", delete "communication" and insert therefor --communicating--.
Col. 13, line 25, after "for" and before "liquid", delete "communication" and insert therefor --communicating--.
Col. 13, line 46, after "force" and before "the", delete "caused" and insert therefor --causes--.
Col. 14, line 10, after "for" and before "liquid", delete "communication" and insert therefor --communicating--.
Col. 14, line 30, after "the" and before "second", delete "grater" and insert therefor --greater--.
Col. 14, lines 60-61, after "for" and before "liquid", delete "communication" and insert therefor --communicating--.

Signed and Sealed this

Thirtieth Day of January, 1996

Attest:

BRUCE LEHMAN

Attesting Officer

Commissioner of Patents and Trademarks